United States Patent [19]
DeSantis, Jr. et al.

[11] Patent Number: 5,320,839
[45] Date of Patent: Jun. 14, 1994

[54] TOPICAL OPHTHALMIC COMPOSITIONS COMPRISING 4-(3-SUBSTITUTED AMINO-2-HYDROXYPROPOXY)-1,2,5-THIADIAZOLES AND METHODS FOR THEIR USE

[75] Inventors: Louis DeSantis, Jr.; Robert J. Adamski, both of Fort Worth, Tex.

[73] Assignee: Alcon Laboratories, Inc., Forth Worth, Tex.

[21] Appl. No.: 104,270

[22] Filed: Aug. 10, 1993

Related U.S. Application Data

[63] Continuation of Ser. No. 939,540, Sep. 2, 1992, abandoned, which is a continuation of Ser. No. 776,544, Oct. 11, 1991, abandoned.

[51] Int. Cl.$^5$ ............... A01N 43/82; A61K 31/41; C07D 417/08; C07D 417/12
[52] U.S. Cl. ............... 424/78.04; 424/78.1; 424/78.37; 424/427; 424/428; 514/362; 514/772.6; 514/777; 514/912; 514/913; 544/134
[58] Field of Search ......... 514/912, 913, 362, 772.6, 514/777; 424/78.04, 78.1, 78.37, 427, 428; 544/134

[56] References Cited

U.S. PATENT DOCUMENTS

| | | | |
|---|---|---|---|
| 3,655,663 | 4/1972 | Wasson | 544/134 |
| 3,657,237 | 4/1972 | Weinstock et al. | 544/134 |
| 3,729,469 | 4/1973 | Wasson | 544/134 |
| 4,195,085 | 3/1980 | Stone | 514/913 |
| 4,521,414 | 6/1985 | Chiou et al. | 514/913 |
| 4,539,317 | 9/1985 | Baldwin et al. | 544/58.7 |
| 4,539,318 | 9/1985 | Baldwin et al. | 544/58.6 |
| 4,623,652 | 11/1986 | Erhardt et al. | 544/58.1 |
| 4,911,920 | 3/1990 | Jani et al. | 514/913 |

FOREIGN PATENT DOCUMENTS

WO84/02525 7/1984 PCT Int'l Appl. .
WO88/07044 9/1988 World Int. Prop. O. .

OTHER PUBLICATIONS

Wasson et al., *J. Med. Chem.*, 15(6):651-655 (1972).
Heel et al., *Drugs*, 17:38-55 (1979).
L. Bonomi et al., "Comparison of the Effects of Nine Beta-Adrenergic Blocking Agents on Intraocular Pressure in Rabbits," *Graefes Archiv Ophthalmologie*, vol. 210, 1:1-8 (1979).
Ph. Dorosz' *Guide Pratique des Medicaments*, 818-819 (1987).
Tocco et al., "Timolol Metabolism in Man and Laboratory Animals," *Drug Metabolism and Disposition*, vol. 8, 4:236-240.

Primary Examiner—Thurman K. Page
Assistant Examiner—Carlos Azpuru
Attorney, Agent, or Firm—Julie J. L. Cheng

[57] ABSTRACT

Topical ophthalmic compositions comprising certain thiadiazoles are useful in the treatment of glaucoma and ocular hypertension. The thiadiazoles are slightly less potent than timolol; however, they have greatly reduced systemic side effects as compared to timolol.

8 Claims, 1 Drawing Sheet

TOPICAL OPHTHALMIC COMPOSITIONS COMPRISING 4-(3-SUBSTITUTED AMINO-2-HYDROXYPROPOXY)-1,2,5-THIADIAZOLES AND METHODS FOR THEIR USE

This application is a continuation of application Ser. No. 07/939,540, filed Sep. 2, 1992, which is a continuation of application Ser. No. 07/776,544, filed Oct. 11, 1991 both now abandoned.

BACKGROUND OF THE INVENTION

This invention relates to topical ophthalmic compositions comprising certain 4-(3-substituted amino-2-hydroxypropoxy)-1,2,5-thiadiazoles. These compounds are β-blockers which are effective at relatively low doses. Ophthalmic compositions comprising these compounds are useful in the treatment of glaucoma and ocular hypertension.

This class of compounds was originally disclosed in German Patent No. 1,925,956 (issued in 1969 to B. K. Wasson), which is equivalent to U.S. No. 3,655,663 (issued in 1972) and U.S. No. 3,729,469 (issued in 1973). It was later found that topical application of timolol, one of the most effective thiadiazoles disclosed and claimed in U.S. No. 3,655,663 (the '663 patent), was also useful to treat ocular hypertension. See, for example, Heel, et al., *Drugs,* 17:38–55 (1979). Although effective in decreasing intraocular pressure, there are often rather severe systemic side effects associated with the use of topical ophthalmic compositions of timolol. Because timolol was the most potent of the compounds tested, other compounds of the class disclosed in the '663 patent were thought to be unsuitable for the treatment of ocular hypertension, as the larger doses which would be needed would be intolerable due to the corresponding increase in systemic and ocular side effects.

SUMMARY OF THE INVENTION

It has now been found that certain of the thiadiazoles of the '663 patent, while being equal or slightly less efficacious than timolol to lower IOP, are far less likely to cause systemic side effects. Moreover, these thiadiazoles are more efficacious than betaxolol. In particular, it has been found that the thiadiazoles of the present invention are approximately four times less potent than timolol to lower IOP, yet they are approximately forty five times less likely to cause systemic side effects. Thus, topical ophthalmic compositions comprising the thiadiazoles of the present invention contain a higher concentration of active than corresponding ophthalmic compositions containing timolol, but cause fewer systemic side effects.

DETAILED DESCRIPTION OF THE INVENTION

Figure 1:
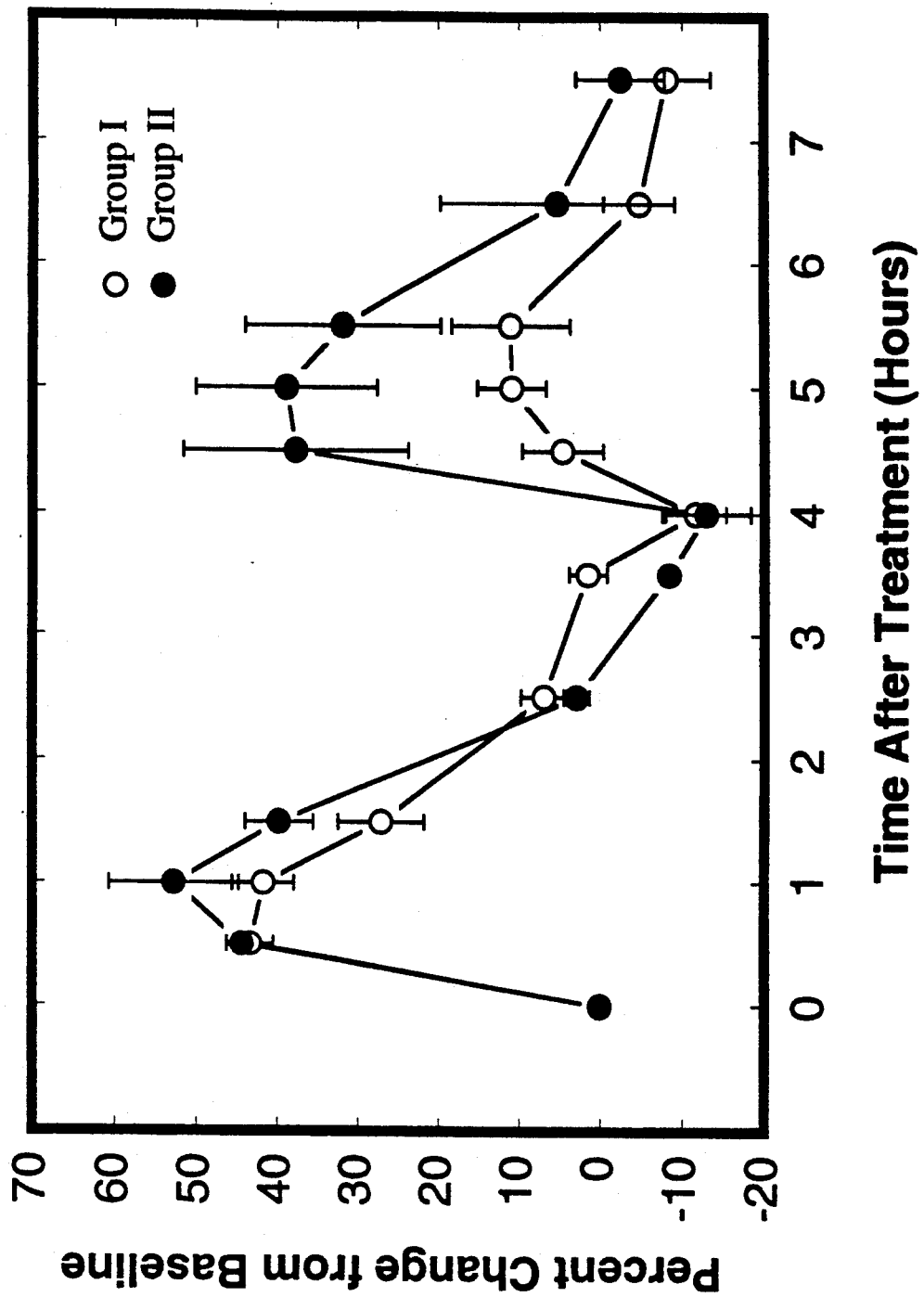
FIG. 1 is a graph of time (hr) versus mean percent change in heart rate (beats per minute).

The thiadiazoles of the present invention have the following general formula:

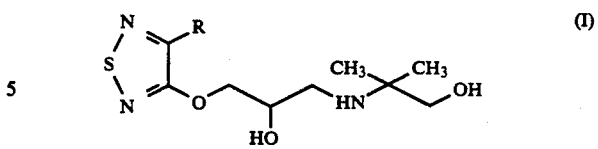

and optically active isomers and pharmacologically acceptable salts thereof; wherein R represents: (1) hydrogen; (2) halogen, preferably chloro or bromo; (3) $C_{1-5}$ lower alkyl having either a straight or branched chain such as methyl, ethyl, propyl, isopropyl, butyl iso-, secondary- or tert-butyl and amyl, including all of its branched chain configurations; (4) $C_{2-5}$ lower alkenyl, such as vinyl, allyl, methallyl and the like; (5) a group having the structure Y—X—Z—, wherein Y is either a straight or branched chain $C_{1-4}$ alkyl optionally substituted with a phenyl group or a phenyl optionally substituted with one or more halogen atoms (especially chloro, bromo, fluoro), hydroxy, $C_{1-3}$ lower alkyl or alkoxy, X is oxygen or sulfur and Z is a $C_{1-2}$ alkyl; (6) a carbamoyl group having the structure RHNCO, wherein $R^1$ is a $C_{1-5}$ lower alkyl; (7) $C_{3-6}$ cycloalkyl, such as cyclopropyl, cyclobutyl, cyclopentyl, cyclohexyl and the like; (8) $C_{1-5}$ lower alkoxy, either a straight or branched chain and including methoxy, ethoxy, propoxy, isopropoxy, butoxy, and pentoxy (the latter groups existing in either straight or branched configuration); (9) phenyl or substituted phenyl, wherein the substitutes are selected from one or more halogen atoms (preferably chloro or fluoro) and a $C_{1-3}$ lower alkyl or alkoxy; (10) phenyl-lower alkyl, wherein the lower alkyl moiety is either a straight or branched chain and has from 1 to 4 carbons and the phenyl moiety can be unsubstituted or substituted with one or more halogen atoms (preferably chloro, fluoro, or bromo) or $C_{1-3}$ lower alkyl or alkoxy; (11) an amino having the structure —$NR^2R^3$, wherein $R^2$ represents hydrogen, $C_{1-4}$ lower alkyl and $C_{2-4}$ hydroxy-substituted lower alkyl, $R^3$ represents hydrogen, $C_{1-4}$ lower alkyl, a hydroxy-substituted lower alkyl and phenyl, or $R^2$ and $R^3$ can be joined together either directly to give a 3 to 7 membered ring with the nitrogen to which they are attached thereby forming aziridinyl, azetidinyl, pyrrolidyl, piperidyl, or a hexahydroazepinyl group, said 3 to 7 membered rings being either unsubstituted or substituted, preferably with one or more $C_{1-5}$ lower alkyl and $C_{1-3}$ hydroxy-lower alkyl, or alternatively $R^2$ and $R^3$ can be joined through an oxygen, nitrogen or sulfur atom to form a 5 or 6 membered ring, advantageously a morphol into, hexahydropyrimidyl, thiazolidinyl, p-thiazinyl, piperazinyl and the like group optionally substituted by $C_{1-3}$ lower alkyl; or (12) R additionally can be a 5 or 6 membered heterocyclic ring having oxygen, nitrogen or sulfur as the hetero atom and preferably the 2-furyl, 2- or 3-thienyl, 2-pyrryl and the o-, m-, or p-pyridyl. These thiadiazoles may be prepared by the methods disclosed in U.S. No. 3,655,663 and U.S. No. 3,729,469 whose entire contents are incorporated by reference herein. Preferred thiadiazoles are those of Formula (I), above, wherein R is chloro, ethyl, allyl, cyclopropyl, ethoxy, phenyl, phenyl-chloromethyl, or 2- (cycl opropylmethoxy)ethyl.

Suitable pharmacologically acceptable salts are acid addition salts derived from inorganic acids, for example, hydrochlorides, hydrobromides, phosphates or sulfates, or salts derived from organic acids, for example, oxalates, lactates, malates, maleates, formates, acetates, succinates, tartrates, salicylates, citrates, phenylacetates, benzoates, p-toluenesulfonates insoluble products which afford a slow release of the active material, for example, a 1,1'-methylene-bis(2-hydroxy-3-naphthoate) and the like.

In general, thiadiazoles are present in the compositions of the present invention at a concentration between about 0.005 and about 5 percent by weight (wt%). It is preferred to have a thiadiazole concentration between about 0.1 and about 2.0 wt%. Most preferably, the thiadiazole concentration is about 1.0 wt%.

The compositions of the present invention may be prepared by combining one or more of the thiadiazoles of the present invention with a suitable vehicle to form a solution, dispersion or gel. These compositions may additionally include finely divided ion exchange resins and/or anionic mucomimetic polymer for enhanced bioavailability and efficacy, as well as for patient comfort. The use of finely divided ion exchange resins and artionic mucomimetic polymers in ophthalmic compositions are detailed in U.S. Pat. No. 4,911,920 (Jani et al.), whose entire contents are hereby incorporated by reference herein.

The compositions of the present invention may also include one or more ingredients conventionally found in ophthalmic formulations, such as preservatives (e.g., benzalkonium chloride or thimerosal), viscosity-imparting agents (e.g., polyvinyl alcohol or hydroxypropyl methylcellulose) and tonicity agents (e.g., sodium chloride or mannitol). The compositions will also normally include buffering agents, such as phosphates and citrates, to maintain the pH within the range of physiological pH (between 6.0 and 7.5). Hydrochloric acid or sodium hydroxide will typically be used to adjust the pH of the resultant composition.

EXAMPLE 1

The following Table I represents some preferred compositions of the present invention.

TABLE 1

| Ingredient | FORMULATION (wt %) | | | | | |
|---|---|---|---|---|---|---|
| | #1 | #2 | #3 | #4 | #5 | #6 |
| (I), R = ethyl | 1.0 | 0.5 | 1.0 | 1.0 | 1.0 | 1.0 |
| Benzalkonium Chloride | 0.01 | 0.01 | 0.01 | 0.01 | 0.01 | 0.01 |
| Amberlite ® IRP-69 resin | 1.0 | 0.5 | 1.0 | — | — | — |
| Mannitol | 4.0 | 4.5 | 4.0 | — | — | — |
| Carbopol ® 934P | 0.5 | 0.25 | 1.0 | — | — | — |
| Sodium Chloride | — | — | — | 0.8 | 0.85 | 0.65 |
| Disodium Phosphate | — | — | — | 0.20 | — | — |
| NaOH and/or HCl | q.s. pH | q.s. pH | q.s. pH | q.s. pH | q.s. pH | q.s. pH |
| Purified Water | q.s. 100% | q.s. 100% | q.s. 100% | q.s. 100% | q.s. 100% | q.s. 100% |

Formulations 1-3, containing finely divided ion exchange resins, may be prepared by first dissolving the drug in water and then slowly dispersing the resin into the solution to form a suspension. Mannitol previously dissolved in an aliquot of water and mixed with benzalkonium chloride is ten added to the suspension. Carbopol ®934P is then added to obtain the desired viscosity. The resultant composition can then be suitably sterilized and filled into previously sterilized containers.

Formulations 4-6 maybe prepared by dissolving the drug in water, along with the other ingredients. Water is then added to bring the solution to 100% and the pH is adjusted. The resultant composition can then be suitably sterilized and filled into suitable packaging for ocular administration.

EXAMPLE 2

A study was conducted to determine the effect on the intraocular pressure of cynomolgus monkeys after a single topical installation of a composition of the present invention.

Prior to the commencement of the study, the right eyes of all of the monkeys had been given laser trabeculoplasty, which resulted in ocular hypertension in the lasered eyes. All of the left eyes were normal and normotensive. The animals had also been trained to sit in "restraint chairs" and conditioned to accept the pressure measurements without general anesthesia.

A total of 14 cynomolgus monkeys (*Macaca fascicularis*) were used in this study. The lasered right eyes of half of the monkeys were given 50 microliters ($\mu$l) of a 1% solution of 3-ethyl-4-[3-N-(2-hydroxymethylprop-2-yl)amino]hydroxypropoxy-1,2,5-thiadiazole (a composition of the present invention) and the lasered right eyes of the other half were given 50 $\mu$l of 0.9% saline. The left eyes of all of the monkeys remained untreated, for comparison purposes. Intraocular pressure (IOP) measurements for both eyes of all of the monkeys were taken just before administration and 1,3 and 6 hours after administration. IOP was determined using an Alcon Pneumatonograph (Alcon Laboratories, Inc., Fort Worth, Tex.) after light corneal anesthesia with proparacaine. Following each measurement, the residual anesthetic was washed out with saline. The results are shown in Table 2, below.

TABLE 2

| Treatment | Time (hr) after dose | % IOP Change | | | |
|---|---|---|---|---|---|
| | | OD | | OS | |
| | | Mean | SEM | Mean | SEM |
| (I), R = ethyl* | 0 | 0.0 | 0.00 | 0.0 | 0.00 |
| | 1 | −25.7 | 4.28 | 1.5 | 3.24 |
| | 3 | −42.0 | 3.18 | 0.6 | 4.73 |
| | 6 | −33.8 | 3.67 | 4.1 | 5.53 |
| Control OD | 0 | 0.0 | 0.00 | 0.0 | 0.00 |
| | 1 | −1.1 | 3.77 | 2.6 | 2.8 |
| | 3 | −13.4 | 5.87 | −4.1 | 4.00 |
| | 6 | −7.0 | 6.74 | 1.9 | 3.91 |

*1% solution

The results demonstrate that the composition of the present invention reduces IOP in hypertensive eyes by more than 25% for a period of at least 6 hours after treatment.

EXAMPLE 3

A study was conducted to determine the effect on the corneal sensitivity of New Zealand albino (NZA) rabbits after a single topical installation of a composition of the present invention. In this study, corneal sensitivity was measured as a function of blink response. The rabbit consistently exhibits a blink of the eyelid when the cornea is touched with sufficient force. This is a protective reflex which is absent when the cornea is anesthetized.

Three NZA rabbits were assigned to each of three test groups. The eyelashes were trimmed and one eye of each animal selected for use. A 1% solution of 3-ethyl-4-[3-N-(2-hydroxymethylprop-2-yl)amino]hydroxypropoxy-1,2,5-thiadiazole (a composition of the present invention) was administered to the selected eye of each animal in one group and either acetate buffered saline or commercially available Timoptic®(Merck, Sharp & Dohme, West to the selected eye of each animal in one group and either acetate buffered saline or commercially available Timoptic (Merck, Sharp & Dohme, West Point, Pa.) were administered to the selected eye of each animal in the other groups.

Corneal sensitivity was measured by tapping the beveled end of a short length of polyethylene tubing on each test eye three times and recording the number of blinks after each tap (maximum=3 blinks/3 taps). Responses were recorded at 15 minute intervals up to ninety minutes after dosing; two baseline measurements were recorded at 15 minute intervals prior to dosing. The results are shown below in Table 3.

TABLE 3

| Treatment (dose) | Rabbit | Eye | Pre-Dose Baseline | \multicolumn{6}{c}{Number of Blinks/Three Touches Minutes (Post-Dose)} |||||| 
|---|---|---|---|---|---|---|---|---|---|
| | | | | 15 | 30 | 45 | 60 | 75 | 90 |
| (I), R = ethyl* | 1 | OD | 3 | 3 | 3 | 2 | 3 | 3 | 3 | 3 |
| | | OS | 3 | 3 | 3 | 3 | 3 | 3 | 3 | 3 |
| | 2 | OD | 3 | 3 | 3 | 3 | 3 | 3 | 3 | 3 |
| | | OS | 3 | 3 | 3 | 3 | 3 | 3 | 3 | 3 |
| | 3 | OD | 3 | 3 | 2 | 3 | 3 | 3 | 3 | 3 |
| | | OS | 3 | 3 | 3 | 3 | 3 | 3 | 3 | 3 |
| Timolol* | 4 | OD | 3 | 3 | 3 | 3 | 3 | 3 | 3 | 3 |
| | | OS | 3 | 3 | 3 | 3 | 3 | 3 | 3 | 3 |
| | 5 | OD | 3 | 3 | 3 | 3 | 3 | 3 | 3 | 3 |
| | | OS | 3 | 3 | 3 | 3 | 3 | 3 | 3 | 3 |
| | 6 | OD | 3 | 3 | 3 | 3 | 3 | 3 | 3 | 3 |
| | | OS | 3 | 3 | 3 | 3 | 3 | 3 | 3 | 3 |
| Vehicle | 7 | OD | 3 | 3 | 3 | 3 | 3 | 3 | 3 | 3 |
| | | OS | 3 | 3 | 3 | 3 | 3 | 3 | 3 | 3 |
| | 8 | OD | 3 | 3 | 3 | 3 | 3 | 3 | 3 | 3 |
| | | OS | 3 | 3 | 3 | 3 | 3 | 3 | 3 | 3 |
| | 9 | OD | 3 | 3 | 3 | 3 | 3 | 3 | 3 | 3 |
| | | OS | 3 | 3 | 3 | 3 | 3 | 3 | 3 | 3 |

*500 μg dose

The results demonstrate that there is no significant difference in corneal sensitivity between any of the formulations administered to the rabbits. Beta blockers which cause complete loss of corneal sensitivity are deemed to be unsafe for chronic use as they remove the protective blink response. This renders the cornea subject to injury if touched with sufficient force by a foreign object.

EXAMPLE 4

A study was conducted to determine the effect on isoproterenol-induced tachycardia in conscious cynomolgus monkeys after a single topical installation of a composition of the present invention.

All of the monkeys used in this study were given laser trabeculoplasty, as detailed in EXAMPLE 2, above, prior to the commencement of the study; however, as hypertensive eyes were not necessary to this study, only the left (normotensive) eyes of the monkeys were studied.

A total of 9 cynomolgus monkeys were used in this study. The left eyes (normotensive) of all of the monkeys were each given a 30 μl aliquot of a 1.5% solution of isoproterenol both immediately after the baseline measurements were taken and again 4 hours later. The monkeys were separated into two study groups: (Group I) 7 were given a 1% solution of 3-ethyl-4-[3-N-(2-hydroxymethylprop-2-yl)amino]hydroxypropoxy-1,2,5-thiadiazole (a composition of the present invention); and (Group II) 2 were given phosphate buffered saline. These solutions were administered to the left eye 3.5 hours after baseline heart rate measurements were taken.

Heart rate was measured with a stethoscope held to the chest of each animal. The beats in two 15 second intervals were recorded and the two recordings averaged. In addition to the baseline measurements, heart rate was measured at 0.5, 1, 1.5, 2.5 and 3.5 hours after baseline and at 0.5, 1, 1.5, 2.5 and 3.5 hours after treatment with beta-blocker or vehicle. The results are shown in Table 4, below, and in FIG. 1.

TABLE 4

| Treatment | TIME (HR) | Heart Rate (beats/minute) | | % Chg from Baseline | |
|---|---|---|---|---|---|
| | | Mean | SEM | Mean | SEM |
| Group I | 0.0 | 136.3 | 4.15 | 0.0 | 0.00 |
| | 0.5 | 195.2 | 6.44 | 43.3 | 2.86 |
| | 1.0 | 192.9 | 6.47 | 41.7 | 3.80 |
| | 1.5 | 172.9 | 8.02 | 27.1 | 5.31 |
| | 2.5 | 145.7 | 6.27 | 6.9 | 2.84 |
| | 3.5 | 138.0 | 3.68 | 1.5 | 2.32 |
| | 4.0 | 120.0 | 5.15 | −11.7 | 3.68 |
| | 4.5 | 142.3 | 7.64 | 4.6 | 5.01 |
| | 5.0 | 151.1 | 7.12 | 10.9 | 4.27 |
| | 5.5 | 150.8 | 10.08 | 11.0 | 7.31 |
| | 6.5 | 129.2 | 5.16 | −4.8 | 4.33 |
| | 7.5 | 124.3 | 5.86 | −8.1 | 5.45 |
| Group II | 0.0 | 142.0 | 10.00 | 0.0 | 0.00 |
| | 0.5 | 205.2 | 15.00 | 44.3 | 0.40 |
| | 1.0 | 216.0 | 4.00 | 52.7 | 7.95 |
| | 1.5 | 198.0 | 8.00 | 39.7 | 4.20 |
| | 2.5 | 146.0 | 8.00 | 2.9 | 1.60 |
| | 3.5 | 130.0 | 10.00 | −8.5 | 0.60 |
| | 4.0 | 123.2 | 1.00 | −13.0 | 5.40 |
| | 4.5 | 194.0 | 6.00 | 37.6 | 13.90 |
| | 5.0 | 196.0 | 2.00 | 38.8 | 11.20 |
| | 5.5 | 186.0 | 4.00 | 31.8 | 12.10 |
| | 6.5 | 148.0 | 10.00 | 5.3 | 14.45 |
| | 7.5 | 138.0 | 2.00 | −2.5 | 5.45 |

The results show that, although the heat rate in both groups increased, the monkeys in group II experienced a greater increase in heart rate than those in Group I (this is best observed in FIG. 1). it therefore appears that topical application of a composition of the present invention partially suppresses isoproterenol-induced tachycardia in conscious cynomolgus monkeys.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating ocular hypertension for those in need thereof comprising administering to an affected eye between about 0.005 and about 5.0 percent by weight of a topical ophthalmic composition comprising a thiadiazole of formula:

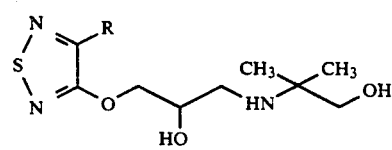

and optically active isomers and pharmacologically acceptable salts thereof, wherein R is selected from the group consisting of: hydrogen, halogen, $C_{1-5}$ alkyl, $C_{2-5}$ mono-alkenyl, $C_{2-5}$ alkoxy, $C_{3-6}$ cycloalkyl, phenyl, phenalkyl, morpholino, furyl, thienyl and pyrryl.

2. The method of claim 1, wherein R is selected from the group consisting of: chlorine, ethyl, allyl, cyclopropyl, ethoxy, phenyl, phenyl -chloromethyl and 2 -cyclopropyl methoxy) ethyl.

3. The method of claim 2, wherein R is ethyl.

4. The method of claim 2, wherein R is 2-(cyclopropylmethoxy)ethyl.

5. The method of claim 1, wherein the thiadiazole is present in an amount between about 0.1 and about 2.0 percent by weight.

6. The method of claim 5, wherein the thiadiazole is present in an amount of about 1.0 percent by weight.

7. The method of claim 1, further comprising an anionic mucomimetic polymer.

8. The method of claim 7, further comprising finely divided ion exchange resin.

* * * * *